(12) United States Patent
Biellak et al.

(10) Patent No.: US 6,577,389 B2
(45) Date of Patent: Jun. 10, 2003

(54) SYSTEM AND METHODS FOR INSPECTION OF TRANSPARENT MASK SUBSTRATES

(75) Inventors: Steve Biellak, Sunnyvale, CA (US); Noah Bareket, Saratoga, CA (US); Stanley E. Stokowski, Danville, CA (US)

(73) Assignee: KLA-Tencor Technologies Corporation, Milpitas, CA (US)

( * ) Notice: Subject to any disclaimer, the term of this patent is extended or adjusted under 35 U.S.C. 154(b) by 0 days.

(21) Appl. No.: 09/888,724

(22) Filed: Jun. 25, 2001

(65) Prior Publication Data

US 2002/0196433 A1 Dec. 26, 2002

(51) Int. Cl.[7] .............................................. G01N 21/00

(52) U.S. Cl. ................ 356/237.4; 356/237.3; 356/239.8

(58) Field of Search .......................... 356/237.3, 237.4, 356/239.8

(56) References Cited

U.S. PATENT DOCUMENTS 6,172,749 B1 * 1/2001 Watanabe ................ 356/237.4
2002/0196433 A1 * 12/2002 Biellak et al. ........... 356/239.1

* cited by examiner

Primary Examiner—Hung Xuan Dang
Assistant Examiner—David N Spector
(74) Attorney, Agent, or Firm—Parsons Hsue & De Runtz LLP.

(57) ABSTRACT

A method for detecting an anomaly on a first surface of a transparent substrate starts with providing a transparent substrate that has a reflective second surface. The method then comprises directing a radiation beam at the first surface of the substrate so that at least a portion of the radiation penetrates the substrate and strikes the reflective second surface. This radiation is reflected back as a reflected radiation beam through the first surface of the substrate. The method then comprises detecting radiation from the reflected radiation beam. This method can further comprise causing relative motion between the radiation beam and the first surface of the substrate. This method can also further comprise documenting the presence of an anomaly if the detected radiation shows that the reflected radiation beam was scattered upon traversing the first surface.

47 Claims, 8 Drawing Sheets

FIG. 8 though of wafer or photomask surface inspection, and more particularly, to illumination and light collection optics for inspecting transparent glass substrates.

SYSTEM AND METHODS FOR INSPECTION OF TRANSPARENT MASK SUBSTRATES

BACKGROUND

1. Field of the Invention

The invention relates generally to the field of wafer or photomask surface inspection, and more particularly, to illumination and light collection optics for inspecting transparent glass substrates.

2. Background Information

Monitoring anomalies, such as pattern defects and particulate contamination, during the manufacture of semiconductor wafers is an important factor in increasing production yields. Numerous types of defects and contamination, especially particles, can occur on a wafer's surface. Determining the presence, location and type of an anomaly on the wafer surface can aid in both locating process steps at which the anomaly occurred and determining whether a wafer should be discarded.

Originally, particles were monitored manually by visual inspection of wafer surfaces. These particles, usually dust or microscopic silicon particles, caused many of the wafer pattern defects. However, manual inspection proved time-consuming and unreliable due to operator errors or an operator's inability to observe certain defects.

To decrease the time required to inspect wafer surfaces, many automatic inspection systems were introduced. A substantial majority of these automatic inspection systems detect particles and other anomalies based on the scattering of light. These systems include two major components: illumination optics and collection-detection optics. Illumination optics generally consists of scanning a wafer surface with a source of radiation, e.g., a laser or white light. Particles present on the wafer's surface scatter incident radiation. The collection optics detect increases in the amount of scattered radiation received, and these increases generally correspond to particles encountered by the illumination optics. This data is reconciled with reference to the known beam position at those moments when the increases in scattered radiation were detected. The data is then converted to electrical signals which can be measured, counted and displayed on a monitor.

Known systems for inspecting wafers that utilize scattered radiation suffer from severe limitations when they are used to inspect transparent articles such as glass mask substrates. One important limitation is that anomalies on transparent substrates generate substantially less scattered radiation than anomalies on non-transparent substrates. There are at least two factors that contribute to this low scattered radiation output. The first is the presence of destructive interference generated between air-side incident and air-side reflected radiation at the surface of the substrate. The second is a substantial reduction in forward scattered radiation that reaches the collection-detection optics.

Forward scattered radiation is radiation that scatters in the same general direction as the radiation from which it originates. For instance, incident radiation that strikes the substrate can generate forward scattered radiation that travels into the substrate. Incident radiation that strikes an anomaly can generate forward scattered radiation that travels past the anomaly and strikes the substrate surface. And radiation that reflects off the substrate surface (reflected radiation) and then strikes an anomaly from below it can generate forward scattered radiation that tends to travel away from the substrate and into the collection-detection optics. Since this last form of forward scattered radiation tends to travel directly into the collection-detection optics, it generally makes up a sizeable portion of the scattered radiation that is collected during a wafer inspection process. Accordingly, the term "forward scattered radiation" as used herein refers primarily to forward scattered radiation generated by reflected radiation striking an anomaly from below it.

When a radiation source is directed at the surface of a transparent substrate, very little of the incident radiation reflects off the surface as reflected radiation. This is because a substantial portion of the incident light penetrates into the transparent substrate. In fact, only around 0% to 10% of the incident radiation reflects off the surface. This substantial reduction in reflected radiation off transparent substrates (as compared to silicon wafers) results in a correspondingly substantial reduction in forward scattered radiation off anomalies that is directed at the collection-detection optics.

In addition to these problems, background noise increases on a transparent substrate because incident light penetrates the substrate and then scatters as it hits the chuck used to hold the substrate in position. So this and all of the above factors significantly reduce the signal-to-noise ratio when known systems inspect transparent substrates, resulting in poor detection of particles. Accordingly, there is a need for an inspection system that can produce stronger scattered light signals with higher signal-to-noise ratios when encountering anomalies present on transparent substrates.

SUMMARY OF THE INVENTION

The disadvantages and problems associated with inspecting transparent articles such as glass mask substrates have been improved using the present invention.

In accordance with an embodiment of the invention, a method for detecting an anomaly on a first surface of a transparent substrate starts with providing a transparent substrate that has a reflective second surface. The method then comprises directing a radiation beam at the first surface of the substrate so that at least a portion of the radiation penetrates the substrate and strikes the reflective second surface. This radiation is reflected back as a reflected radiation beam through the first surface of the substrate. The method then comprises detecting radiation from the reflected radiation beam. This method can further comprise causing relative motion between the radiation beam and the first surface of the substrate. This method can also further comprise documenting the presence of an anomaly if the detected radiation shows that the reflected radiation beam was scattered upon traversing the first surface.

In accordance with another embodiment, the above method can further comprise directing a second radiation beam at a location on the first surface of the substrate that corresponds to where the reflected radiation beam traverses the first surface, and detecting radiation from the second radiation beam.

In accordance with another embodiment, a method for detecting an anomaly on a first surface of a transparent substrate comprises directing a radiation beam at a second surface of the substrate so that at least a portion of the radiation beam penetrates the substrate and traverses the first surface, and detecting radiation from the radiation beam as it traverses the first surface.

In accordance with another embodiment of the invention, a system for detecting an anomaly on a first surface of a transparent substrate comprises a radiation source operable to emit radiation, an objective operable to focus the radiation into a radiation beam, and a detector mounted to detect radiation. The objective is mounted to direct the radiation beam onto a first location on the first surface of the substrate so that at least a portion of the radiation beam penetrates the substrate and strikes a reflective second surface of the substrate, thereby reflecting the radiation beam back through a second location on the first surface of the substrate.

In accordance other embodiments, the above system can further comprise any one or all of a compensatory plate operable to correct any aberration introduced by the substrate, a collector operable to collect radiation and focus the radiation onto the detector, and/or an optical element operable to redirect the radiation beam to the second location on the first surface of the substrate.

An important technical advantage of the present invention includes reflecting the radiation beam off the reflective second surface of the substrate so that the radiation beam strikes anomalies from the substrate side, rather than from the air side. The use of substrate side radiation increases the sensitivity of the system by reducing radiation loss, reducing interference between scattered and reflected radiation by eliminating collection of the reflected radiation component, reducing background noise, and greatly increasing the amount of forward scattered radiation generated by the system. Another advantage of the invention is that the methods disclosed herein can be performed without significant design changes to current wafer inspection systems and wafer mounting systems.

Other important technical advantages of the present invention are readily apparent to one skilled in the art from the following figures, descriptions, and claims.

BRIEF DESCRIPTION OF THE DRAWINGS

For a more complete understanding of the present invention and for further features and advantages, reference is now made to the following description taken in conjunction with the accompanying drawings, in which.

DETAILED DESCRIPTION OF THE PREFERRED EMBODIMENTS

The preferred embodiments of the present invention and their advantages are best understood by referring to FIGS. 1 through 8 of the drawings. Like numerals are used for like and corresponding parts of the various drawings.

Figure 1:
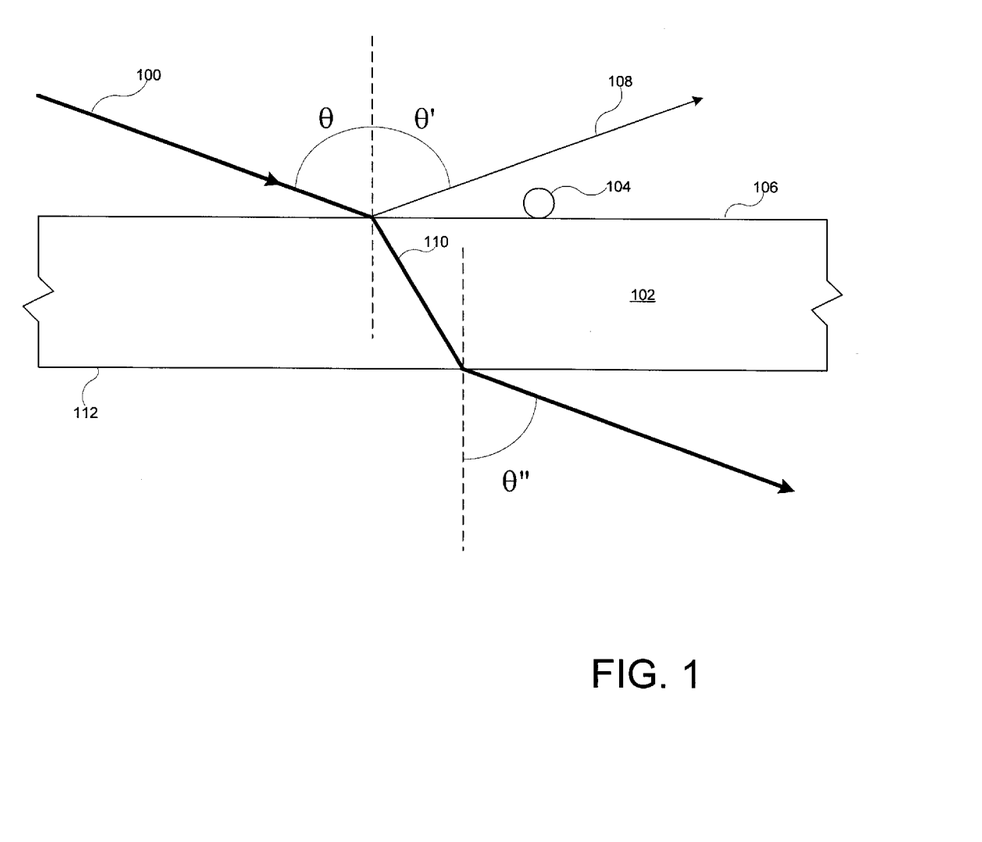
FIGS. 1 and 2 demonstrate a method for inspecting a surface of a substrate where a radiation beam is directed at the surface of the substrate, and a particle is detected when the radiation beam is scattered by the particle.
Figure 2:
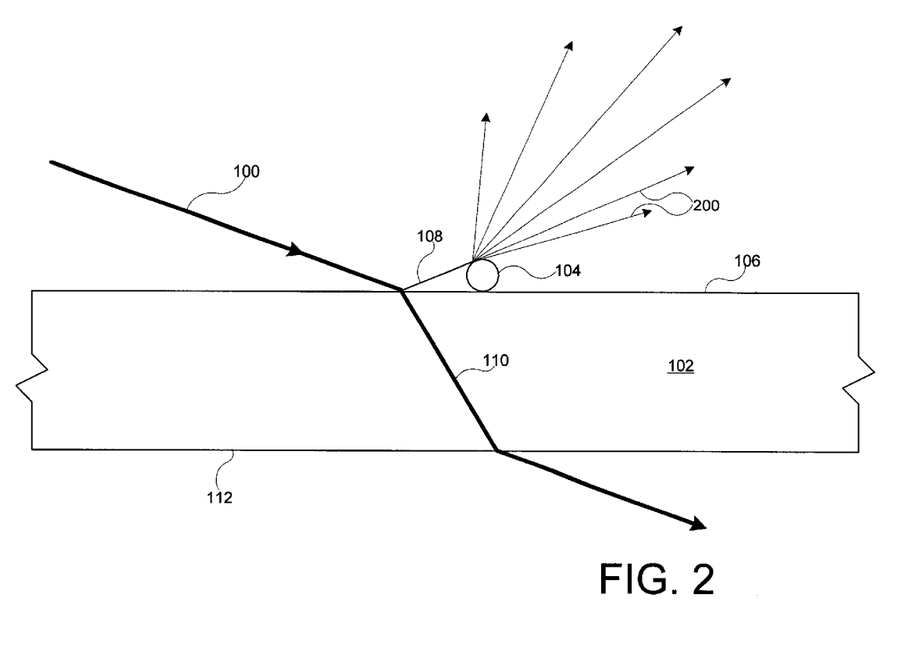

FIGS. 1 and 2 demonstrate a method for detecting particles on the surface of a substrate using a wafer inspection system. For purposes of this description, any reference to "particles" is intended to include other types of anomalies as well, including crystal-originated particles (COPs), which are surface breaking defects in a semiconductor wafer that have in the past been classified as "particles" due to the inability of earlier inspection systems to distinguish them from real particles. FIG. 1 illustrates an instance where an incident radiation beam 100 is directed at a transparent or glass substrate 102 to inspect its surface and does not encounter any particles. Incident radiation beam 100 can be in the form of light, and in particular, a laser beam. Common types of laser beams used for detecting particles include Argon-Ion lasers which can emit radiation at around 488 nm and 514 nm, and solid-state YAG lasers which can emit radiation at around 266 nm, 355 nm, or 1064 nm. Incident radiation beam 100 is generally scanned across the surface of a substrate to look for particles.

Incident radiation beam 100 strikes a first surface 106 at an angle of incidence θ. In an embodiment of the invention, angle θ is equal to around 70 degrees, which is the same angle of incidence used by known semiconductor wafer inspection systems such as the Surfscan® SP1$^{TBI}$ Wafer Inspection Tool by KLA-Tencor of San Jose, Calif.

FIG. 1 includes a particle 104 resting on first surface 106 of substrate 102 and away from incident radiation beam 100. First surface 106 of substrate 102 is also referred to herein as top surface 106. Particles typically found on substrate surfaces, and on semiconductor wafer surfaces in particular, include microscopic particles such as microscopic silicon particles (e.g. Si, $SiO_2$, or $Si_3N_4$), or dust particles. In FIG. 1, particle 104 can also be a polystyrene latex sphere (PSL). This is one type of man-made particle generally used to calibrate tools such as particle deposition systems and wafer scanners.

When incident radiation beam 100 strikes top surface 106, a component of incident radiation beam 100 is reflected off top surface 106 as a reflected radiation beam 108, and another component is transmitted into substrate 102 as a refracted radiation beam 110. Reflected radiation beam 108 has an angle of incidence θ' measured from normal and this incidence angle is equal to the incidence angle θ for incident radiation beam 100. Because substrate 102 is transparent, much of the energy in incident radiation beam 100 is transmitted into substrate 102. Thus, reflected radiation beam 108 generally contains only a small portion of the energy from incident radiation beam 100, typically only between 0% to 10% of the energy.

Refracted radiation beam 110 is refracted as it enters substrate 102. Refracted radiation beam 110 then travels through substrate 102 and exits out a second surface 112 of substrate 102 where it is refracted once again, at an angle of incidence θ' as measured from normal. This angle θ" is equal to angle θ for incident radiation beam 100 and θ' of reflected radiation beam 108. Unlike reflected radiation beam 108, refracted radiation beam 110 generally carries a substantially large portion (between 90% to 100%) of the energy from incident radiation beam 100. Second surface 112 of substrate 102 is also referred to herein as bottom surface 112.

Most of the remaining energy from incident radiation beam 100 is exhausted in different ways, for example, as scattered radiation, by absorption into substrate 102, or as dissipated heat energy. Scattered radiation can be generated at several locations, including where incident radiation beam 100 strikes top surface 106 and where refracted radiation beam 110 strikes bottom surface 112.

FIG. 2 illustrates an instance where particle 104 is detected. Here, portions of incident radiation beam 100 and reflected radiation beam 108 are now scattered by particle 104. The resulting scattered radiation 200 is then collected by the collection-detection optics of the wafer inspection system (shown in FIG. 8). A substantial portion of the scattered radiation 200 that is collected by the system originates from reflected radiation beam 108. This is because reflected radiation beam 108 strikes particle 104 from below, and the resulting forward scattered radiation 200 tends to travel directly into the collection-detection optics of the system.

The collection-detection optics of the system consist of a collector 812 and a detector 814 (both shown in FIG. 8), and are used to collect and detect scattered radiation 200. It is detector 814 that records increases in the level of scattered radiation 200 collected that correspond to particles 104 being found by radiation beams 100 and 108. Normally, detector 814 continually receives a low threshold level of scattered radiation due to scattered radiation being generated by incident beam 100 striking top surface 106 and refracted beam 110 striking bottom surface 112. Therefore, it is typically the increases in the level of scattered radiation collected that indicate a particle has been found.

The amount of scattered radiation 200 generated in FIG. 2 during the inspection of transparent substrate 102 is relatively small compared to the amount generated during the inspection of non-transparent silicon wafers. Again, this is because reflected radiation beam 108, which generates a substantial portion of the detected scattered radiation, contains only 0% to 10% of the energy of incident radiation beam 100 when a transparent surface is being inspected. In addition, deconstructive interference between incident radiation beam 100 and reflected radiation beam 108 further decreases the energy level of reflected radiation beam 108. Accordingly, only a relatively small amount of forward scattered radiation can be generated. This decrease in the level of scattered radiation 200 unfortunately results in decreased system sensitivity.

Figure 3:
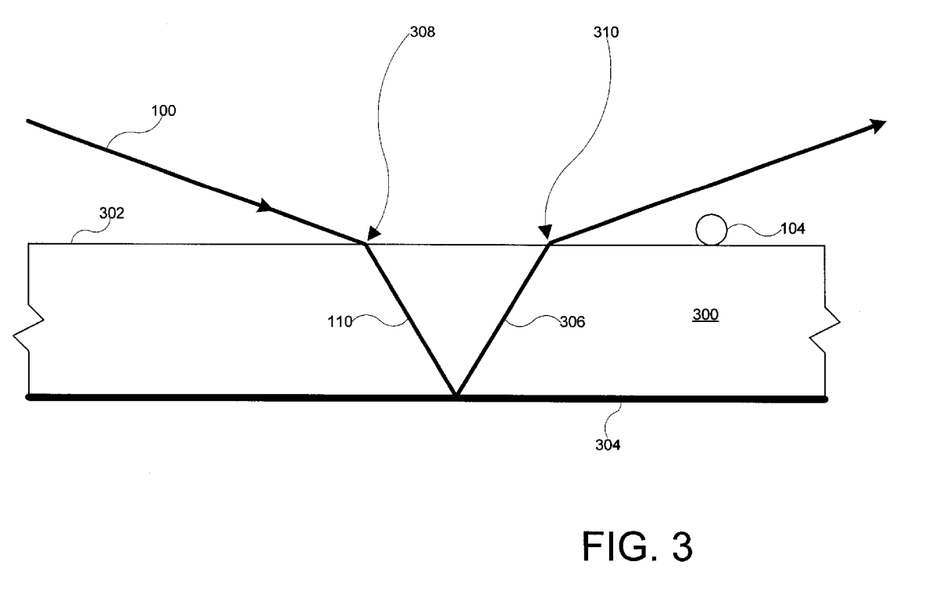
FIGS. 3 and 4 demonstrate a method for inspecting the surface of a substrate in accordance with an embodiment of the invention using substrate-side radiation produced by reflecting radiation off a reflective bottom surface of the substrate.
Figure 4:
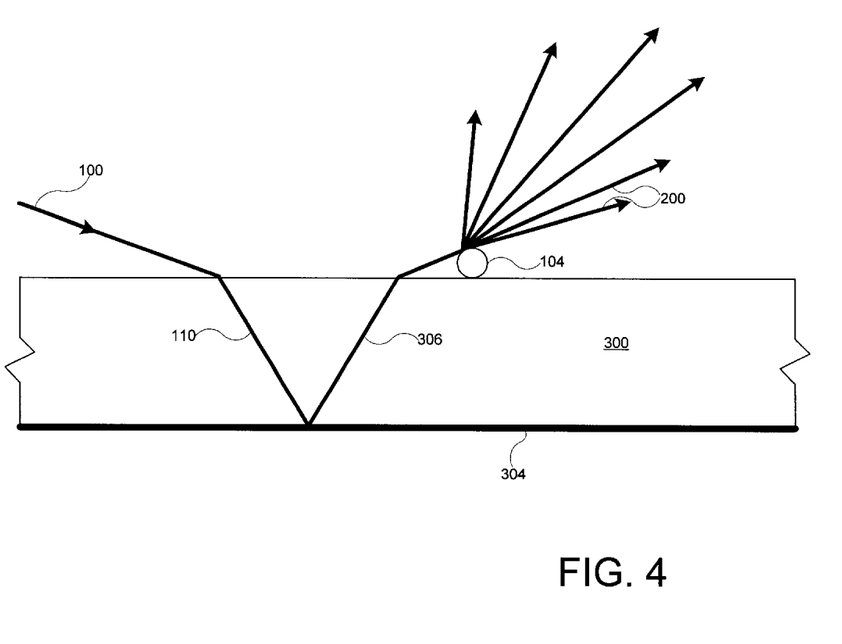

FIGS. 3 and 4 demonstrate an exemplary method for detecting particles on the surface of a substrate in accordance with an embodiment of the invention. Here, particle detection is performed using substrate-side radiation, as opposed to air-side radiation. In particular, the radiation beam used to detect particles in this embodiment travels through substrate 102 prior to striking the particle, as opposed to traveling just through the air as in FIG. 1. In the embodiment of FIGS. 3 and 4, this is accomplished using a modified substrate 300 having a first surface 302 that is being inspected and a second surface 304 that has been made reflective. First surface 302 is also referred to herein as top surface 302, and second surface 304 is also referred to herein as bottom surface 304. The use of reflective bottom surface 304 causes refracted radiation beam 110 to reflect back up towards top surface 302 as a reflected radiation beam 306. It is reflected radiation beam 306 that is now used to detect particle 104 on top surface 302.

Modified substrate 300 is different from substrate 102 only in that bottom surface 304 has been made reflective. In one embodiment, this modification can be done by taking substrate 102 and coating bottom surface 112 with a reflective layer, for instance, by using an aluminization process as is used in extreme ultraviolet (EUV) lithography to enable electrostatic chucking. The use of reflective bottom surface 304 enables the radiation source to remain above top surface 302. This allows the methods of the invention to be implemented on existing wafer inspection systems that use top side, obliquely directed radiation, without the need for having substantial modifications made to them. The primary modification is displacing the optical axis of incident radiation beam 100 so that reflected radiation beam 306 is now focused onto the location of interest.

The use of substrate-side radiation provides several advantages that result in a considerably large increase in the amount of scattered radiation generated off particle 104. One advantage is that substrate-side radiation strikes particle 104 from below at angles that generate forward scattered radiation 200 directed at the collection-detection optics, similar to reflected radiation beam 108. Unlike reflected radiation beam 108, however, substrate-side radiation retains a majority of the energy from incident radiation beam 100, and therefore generates substantially more forward scattering radiation.

Another advantage of substrate-side radiation is that as the substrate-side radiation traverses the top surface of a substrate, constructive interference occurs at the point where the radiation crosses from substrate to air. This constructive interference tends to intensify the radiation leaving the substrate, sometimes intensifying it by 40–60% at certain angles of incidence. This increase in the intensity of the radiation also aids in generating more scattered radiation.

FIG. 3 illustrates a moment where incident radiation beam 100 is directed at substrate 300 to inspect top surface 302 and does not encounter particle 104. Incident radiation beam 100 strikes top surface 302 at a first location 308 where a component of incident radiation beam 100 is refracted into substrate 300 as refracted radiation beam 110. In an embodiment, incident radiation beam 100 has an angle of incidence that is around 70 degrees, as it can have when existing systems are used. Refracted radiation beam 110 then travels through substrate 300 and strikes reflective bottom surface 304 where it is reflected back as reflected radiation beam 306. Reflected radiation beam 306 then travels through substrate 300 and traverses top surface 302 at a second location 310 where it is refracted once again.

It should be noted that when incident radiation beam 100 strikes top surface 302, reflected radiation beam 108 and scattered radiation (not shown) are still produced, as is scattered radiation (not shown) from refracted radiation beam 110 striking bottom surface 304. Detection of these components by the detector (shown in FIG. 8), which tends to interfere with the results obtained, can be minimized or eliminated, as is discussed below with reference to FIG. 8. Thus, these components are not discussed here, or illustrated in FIG. 3, for clarity.

FIG. 4 illustrates a moment where incident radiation beam 100 is directed at substrate 300 to inspect its top surface 302 and reflected radiation beam 306 encounters particle 104. As in FIG. 3, incident radiation beam 100 is directed at top surface 302 at first location 308, and a component enters substrate 300 as refracted radiation beam 110. Refracted radiation beam 110 then travels through substrate 300 and reflects of reflective bottom surface 304 as reflected radiation beam 306. Reflected radiation beam 306 then travels through substrate 300 and traverses top surface 302 where it strikes particle 104. Constructive interference can occur as reflected radiation beam 306 traverses top surface 302, thereby amplifying the intensity of reflected radiation beam 306. As shown in FIG. 4, scattered radiation 200 is then generated off particle 104, and this scattered radiation 200 can be collected and detected by collector 812 and detector 814 (shown in FIG. 8).

Figure 5A:
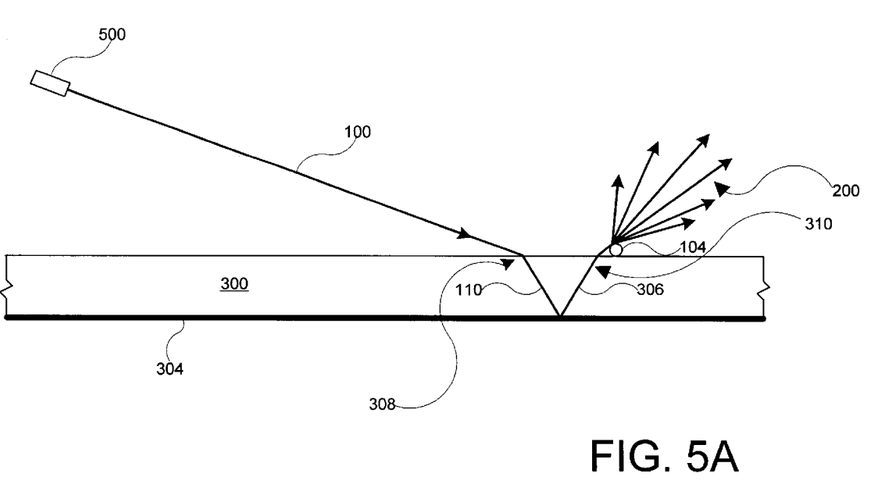
FIGS. 5A and 5B illustrate a system and method in accordance with an alternative embodiment of the invention where a first radiation beam is operable to perform substrate-side inspection of the surface of a substrate and a second radiation beam is operable to perform air-side inspection of the surface of a substrate.
Figure 5B:
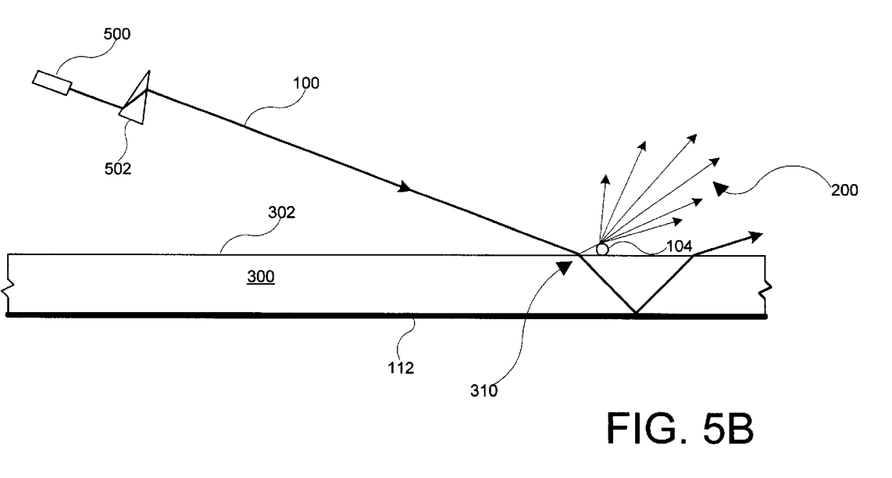

FIGS. 5A and 5B illustrate a system and method designed in accordance with an alternative embodiment of the invention where a first radiation beam is operable to perform substrate-side inspection of the surface of a substrate and a second radiation beam is operable to perform air-side inspection of the surface of a substrate. FIG. 5A illustrates a first step of this alternative embodiment where particle inspection is performed in accordance with the invention, in particular, using reflected radiation beam 306 to detect particle 104. FIG. 5A includes a radiation source 500 that emits incident radiation beam 100 at first location 308 of top surface 302. Then, as described above in FIGS. 3 and 4, a component of incident radiation beam 100 enters substrate 300 as refracted radiation beam 110, refracted radiation beam 110 reflects off reflective bottom surface 304 as reflected radiation beam 306, and reflected radiation beam 306 traverses top surface 302 where it strikes particle 104.

FIG. 5B illustrates a second step of this alternative embodiment where an optical element 502, which can be provided by an objective or a prism (as shown in FIG. 5B), is introduced into the path of incident radiation beam 100. The presence of optical element 502 alters the path of incident radiation beam 100 so that is now strikes top surface 302 at second location 310. Therefore, second location 310 is undergoing substrate-side inspection by reflected radiation beam 306 in FIG. 5A, and air-side inspection by incident radiation beam 100 in FIG. 5B. Through inspection of second location 310 using both air-side and substrate-side inspection techniques, one can discern what type of defect particle 104 is by analyzing the differences in scattered radiation 200 received during the air-side and substrate-side inspections.

Figure 6:
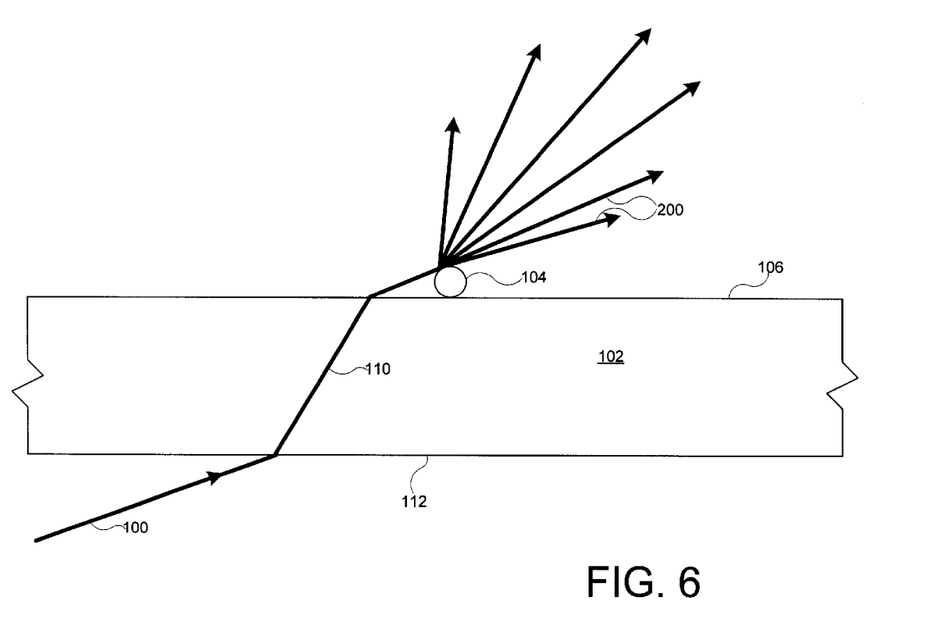
FIG. 6 demonstrates a method for performing substrate-side inspection of a surface of a substrate without the use of a reflective bottom surface in accordance with an alternative embodiment of the invention.

FIG. 6 demonstrates a method for performing substrate-side inspection of a surface of a substrate without the use of a reflective bottom surface in accordance with an alternative embodiment of the invention. Here, rather than providing a reflective bottom surface 304 for refracted radiation beam 110 to reflect off, incident radiation beam 100 is directed from below and directly strikes the substrate on its bottom surface 112. In this embodiment, substrate 102 from FIGS. 1 and 2 is utilized because a reflective bottom surface is no longer necessary. A component of incident radiation beam 100 enters substrate 102 as refracted radiation beam 110, and refracted radiation beam 110 travels through substrate 102 and traverses top surface 106 where it strikes particle 104. Then as before, scattered radiation 200 is collected by collector 812 (shown in FIG. 8) that is still positioned above top surface 106. Thus, substrate-side inspection is performed here without the use of a reflective bottom surface.

Figure 7:
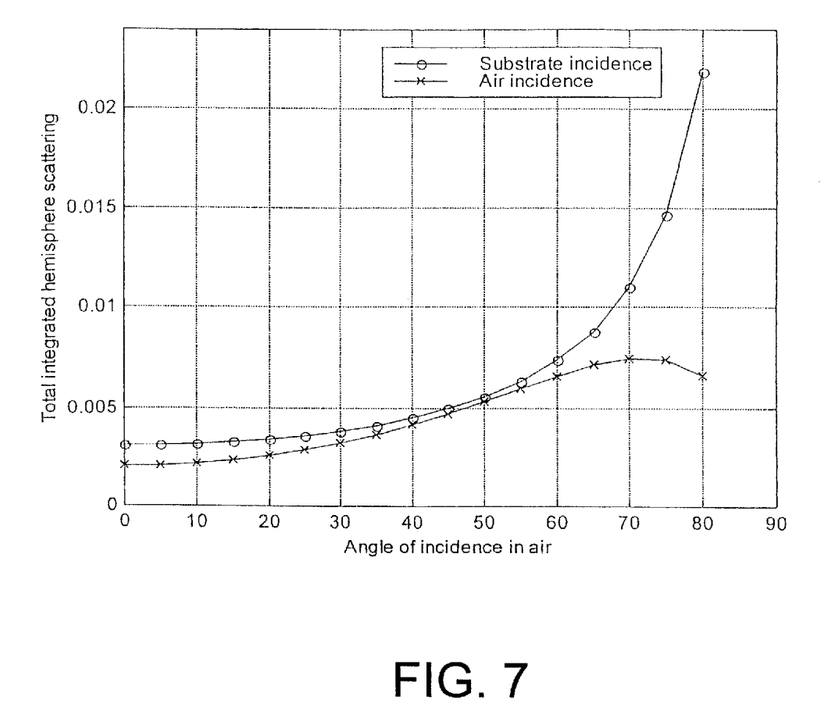
FIG. 7 is a chart that illustrates a difference between substrate-side illumination and air-side illumination for different angles of incidence of the radiation beam.

FIG. 7 is a chart that illustrates the difference between substrate-side illumination and air-side illumination for different angles of incidence of the radiation beam. As shown in FIG. 7, at angles of incidence below 30 degrees and above 60 degrees, much more scattered radiation is detected using substrate-side radiation than using air-side radiation. Most importantly, at an angle of incidence of 70 degrees, which is the angle of incidence used by most known wafer inspection systems, there is substantially more scattered radiation detected when using substrate-side radiation.

Figure 8:
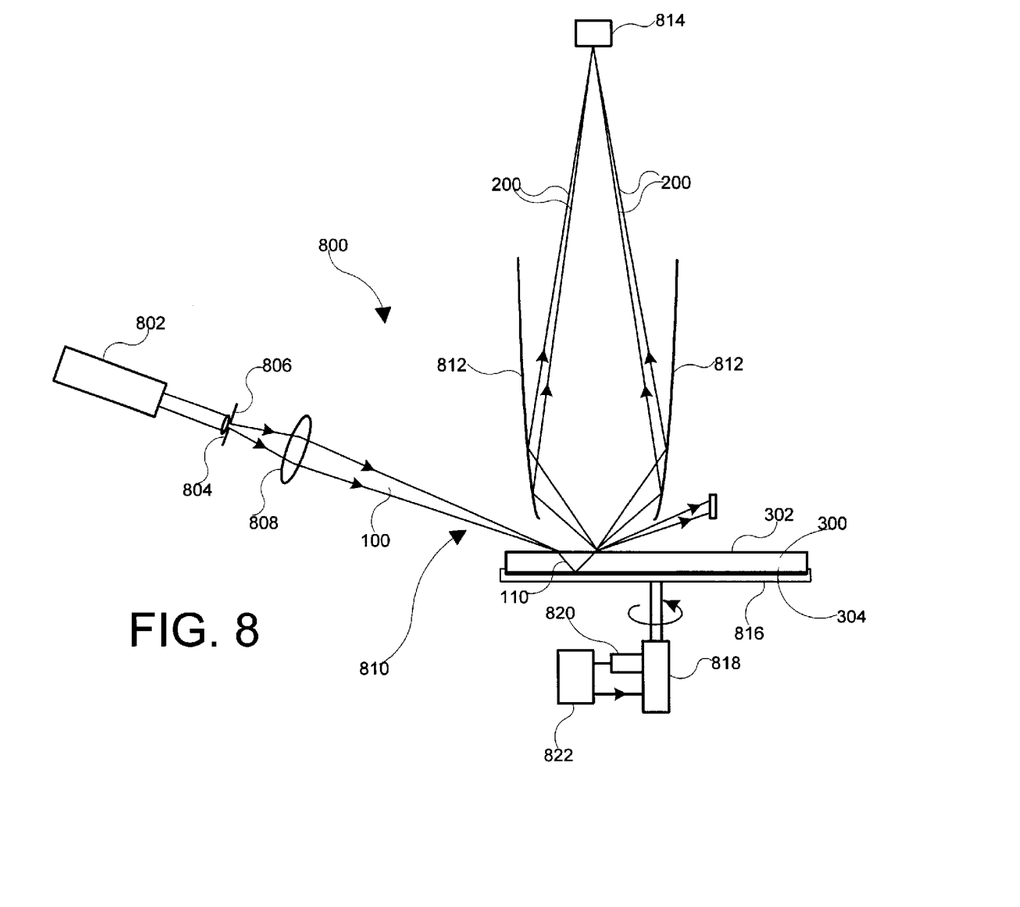
FIG. 8 illustrates a substrate inspection system constructed in accordance with an embodiment of the invention.

FIG. 8 is a schematic view of a sample inspection system 800 according to an embodiment of the invention. Sample inspection system 800 includes a radiation source 802 that operates to emit incident radiation beam 100 at one or more wavelengths. As described above, one device that can be used as radiation source 802 is a solid-state laser. Solid-state lasers tend to be more stable, reliable, and compact than other types of lasers, making them attractive for use in sample inspection systems.

In particular, a YAG solid-state laser can be used as radiation source 802. A YAG laser generally operates by generating radiation at one frequency, and then shifting that frequency to a desired frequency by passing the radiation through Yttrium Aluminum Garnet crystals that are doped with neodymium or erbium. This process is called harmonic laser light generation. The crystals can double, triple, or quadruple the frequency of the radiation. So if the radiation begins at 1064 nanometers (nm), then harmonic laser light generation can produce radiation at 532 nm radiation, 355 nm radiation, or 266 nm radiation. In alternative laser sources, materials such as gas, plasma, or other types of crystals can be used in place of the YAG crystals in the harmonic laser light generation process. In other embodiments of the invention, radiation source 802 can be provided by these alternative laser sources, including Argon Ion lasers.

Sample inspection system 800 can include a lens 804 that can focus incident radiation beam 100 through a pinhole filter 806. This lens-pinhole assembly is a spatial filter that is used to remove spatial noise from incident radiation beam 100, which consists of random fluctuations in the intensity profile of a radiation beam caused by particles and other objects that the radiation beam encounters. These particles tend to degrade the spatial coherence of the radiation beam.

After incident radiation beam 100 passes through lens 804 and filter 806 of the spatial filter, it is focused by lens 808 into oblique illumination channel 810. Incident radiation beam 100 then strikes top surface 302 of glass substrate 300 at an oblique angle, and in an embodiment, this angle is around 70 degrees measured from normal to the substrate surface. As incident radiation beam 100 strikes surface 302, refracted radiation beam 110 enters substrate 300 and is reflected off reflective bottom surface 304. This creates reflected radiation beam 306 that is then used for detecting particles on top surface 302.

In another embodiment, system 800 can include a compensatory plate (not shown) that is mounted between lens 808 and top surface 302. The use of a compensatory plate corrects significant third order aberrations that can be introduced by transparent substrate 300, thereby producing a small illumination spot on top surface 302 for detecting particles.

A portion of scattered radiation 200 generated by reflected radiation beam 306 as it traverses top surface 302 is collected by a collection system 812, provided in this embodiment by an ellipsoidal mirror. The scattered radiation is also focused by collection system 812 onto a detector 814. In an embodiment, detector 814 can be provided by a photomultiplier tube. Collection system 812 and detector 814 can be identical to what is used in known systems, such as the Surfscan® SP1$^{TBI}$ tool by KLA-Tencor described above.

In an embodiment of the invention, collection system 812 can include a field stop to prevent any unwanted scattered radiation components from entering detector 814 and degrading the sensitivity of system 800. This can include scattered radiation created by incident radiation beam 100 striking first location 308 on top surface 302 and/or refracted radiation beam 110 striking reflective bottom surface 304 of substrate 300.

As shown in FIG. 8, glass substrate 300 is mounted onto a chuck 816 which is rotated by a motor 818. Mounting chuck 816 is preferably an edge support chuck, similar to what is currently used in known systems. These elements are then moved linearly by a transducer 820. Both movements are controlled by a controller 822, so that incident radiation beam 100 and reflected radiation beam 306 can scan surface 302 along a spiral scan to cover the entire surface.

In alternate embodiments of the invention, instead of using an ellipsoidal mirror as collection system 812, other curved mirrors or objectives can be used, including but not limited to a paraboloidal mirror. A paraboloidal mirror will collimate the scattered radiation from surface 302 into a collimated beam, and this collimated beam can then be focused by a lens to detector 814. Curved mirrored surfaces having shapes other than ellipsoidal or paraboloidal shapes may also be used.

Accordingly, systems and methods of the invention have been described for inspection of transparent glass substrates. Unlike previously developed techniques in which systems suffered from severe limitations and collected poor data when inspecting transparent substrates, the systems and methods of the present invention utilize substrate-side inspection techniques that can overcome these limitations and provide improved data and greater signal-to-noise ratios. In particular, substrate-side radiation produces greater forward scattered radiation off anomalies on transparent substrates. Also, because the incident radiation beam is offset from the reflected radiation beam as it traverses the top surface, there is no destructive interference between the two. Rather, there is constructive interference as the reflected radiation beam crosses into the air out of the substrate. In addition, the systems and methods of the invention can provide both substrate-side and air-side inspections to aid in defect discrimination. The methods of the invention can even be implemented on existing systems with only minor modifications needed.

While various embodiments of the invention have been shown and described, it will be apparent to those skilled in the art that numerous alterations may be made without departing from the inventive concepts presented herein. Thus, the invention is not to be limited except in accordance with the following claims and their equivalents.

What is claimed is:

1. A method for detecting an anomaly on a first surface of a transparent substrate, comprising:

providing the transparent substrate with a reflective second surface;

directing a radiation beam at the first surface of the substrate so that at least a portion of the radiation beam penetrates the substrate and strikes the reflective second surface, thereby reflecting the radiation beam back as a reflected radiation beam through the first surface of the substrate; and detecting radiation from the reflected radiation beam.

2. The method of claim 1, further comprising causing relative motion between the radiation beam and the first surface of the substrate.

3. The method of claim 1, further comprising documenting the presence of a particle if the detected radiation shows that the reflected radiation beam was scattered upon traversing the first surface.

4. The method of claim 1, further comprising:

directing a second radiation beam at a location on the first surface of the substrate corresponding to where the reflected radiation beam traverses the first surface; and detecting radiation from the second radiation beam after it has interacted with the substrate.

5. The method of claim 1, wherein the radiation beam comprises a light beam.

6. The method of claim 1, wherein the radiation beam comprises a laser beam.

7. The method of claim 1, wherein the radiation beam is polarized.

8. The method of claim 1, wherein the radiation beam is obliquely incident on the first surface.

9. The method of claim 1, wherein the radiation beam is incident on the first surface at an angle around 70 degrees measured from normal.

10. The method of claim 1, wherein the detecting radiation comprises detecting scattered radiation and avoiding reflected radiation off the first surface.

11. The method of claim 2, further comprising documenting the presence of a particle if the detected radiation shows an increase in the amount of scattered radiation produced by the reflected radiation beam.

12. The method of claim 4, further comprising causing relative motion between the second radiation beam and the first surface of the substrate.

13. The method of claim 4, further comprising documenting the presence of a particle if the detected radiation shows that the second radiation beam was scattered upon interacting with the first surface of the substrate.

14. The method of claim 4, further comprising comparing the radiation detected from the reflected radiation beam to the radiation detected from the second radiation beam to determine what type of particle was detected.

15. The method of claim 4, wherein the radiation beam is at a first wavelength and the second radiation beam is at a second wavelength.

16. The method of claim 4, wherein the second radiation beam comprises a laser beam.

17. The method of claim 4, wherein the second radiation beam is obliquely incident on the first surface.

18. The method of claim 12, further comprising documenting the presence of a particle if the detected radiation shows an increase in the amount of scattered radiation produced by the second radiation beam.

19. A method for detecting a particle on a first surface of a transparent substrate in a medium, said substrate having a refractive index higher than that of the medium, comprising:

directing a radiation beam at a second surface of the substrate so that at least a portion of the radiation beam penetrates the substrate and traverses the first surface at an incidence angle such that there is substantially no total internal reflection of the beam by the first surface; and detecting radiation from the radiation beam as it traverses the first surface.

20. The method of claim 19, further comprising causing relative motion between the radiation beam and the second surface of the substrate to detect particles at a plurality of locations.

21. The method of claim 19, further comprising documenting the presence of a particle if the detected radiation shows that the radiation beam was scattered upon traversing the first surface.

22. The method of claim 19, wherein the radiation beam comprises a light beam.

23. The method of claim 19, wherein the radiation beam comprises a laser beam.

24. The method of claim 19, wherein the radiation beam is polarized.

25. The method of claim 19, wherein the radiation beam is obliquely incident on the second surface.

26. The method of claim 20, further comprising documenting the presence of a particle if the detected radiation shows an increase in the amount of scattered radiation produced by the radiation beam.

27. A method for detecting a particle on a first surface of a transparent substrate, comprising:

providing a transparent substrate with a reflective second surface;

directing a radiation beam at the first surface of the substrate so that at least a portion of the radiation beam penetrates the substrate and strikes the reflective second surface, thereby reflecting the radiation beam back as a reflected radiation beam through the first surface of the substrate;

detecting radiation from the reflected radiation beam;

causing relative motion between the radiation beam and the first surface of the substrate; and documenting the presence of a particle whenever there is an increase in the amount of scattered radiation detected.

28. The method of claim 27, further comprising:

directing a second radiation beam at a location on the first surface of the substrate corresponding to where the reflected radiation beam traverses the first surface;

detecting radiation from the second radiation beam; and documenting the presence of a particle whenever there is an increase in the amount of radiation detected from the second radiation beam.

29. The method of claim 28, wherein the radiation beam is at a first wavelength and the second radiation beam is at a second wavelength.

30. A method for detecting a particle on a first surface of a transparent substrate, comprising:

providing a transparent substrate with a reflective second surface;

directing a radiation beam at the first surface of the substrate so that at least a portion of the radiation beam penetrates the substrate and strikes the reflective second surface, thereby reflecting the radiation beam back as a reflected radiation beam through the first surface of the substrate; and detecting radiation from the reflected radiation beam without detecting radiation reflected by the first surface of the substrate.

31. A method for detecting a particle on a first surface of a transparent substrate, comprising:

providing the transparent substrate with a reflective second surface;

directing a radiation beam at the first surface of the substrate so that at least a portion of the radiation beam penetrates the substrate and strikes the reflective second surface, thereby reflecting the radiation beam back as a reflected radiation beam through the first surface of the substrate; and detecting scattered radiation from the reflected radiation beam without detecting reflected radiation from the reflected radiation beam.

32. A system for detecting a particle on a first surface of a transparent substrate, comprising:

a radiation source operable to emit radiation;

an objective operable to focus the radiation into a radiation beam and mounted to direct the radiation beam onto a first location on the first surface of the substrate so that at least a portion of the radiation beam penetrates the substrate and strikes a reflective second surface of the substrate, thereby reflecting the radiation beam back through a second location on the first surface of the substrate; and a detector device positioned to detect radiation reflected from the second surface.

33. The system of claim 32, further comprising a compensatory plate operable to correct aberration introduced by the substrate.

34. The system of claim 32, further comprising a collector operable to collect radiation and focus the radiation onto the detector.

35. The system of claim 32, further comprising an optical element operable to redirect the radiation beam to the second location on the first surface of the substrate.

36. The system of claim 32, the detector device further comprising a field stop mounted to substantially prevent scattered light created by the radiation beam striking the first location on the first surface of the substrate from reaching the detector.

37. The system of claim 32, the detector device further comprising a field stop mounted to substantially prevent scattered light created by the radiation beam striking the reflective second surface of the substrate from reaching the detector.

38. The system of claim 32, further comprising a field stop mounted to substantially prevent scattered light created by the radiation beam striking both the first location on the first surface of the substrate and the reflective second surface of the substrate from reaching the detector.

39. The system of claim 32, wherein the radiation source and the objective are provided by a laser source.

40. The system of claim 32, wherein the detector is mounted to collect scattered radiation and avoid reflected radiation.

41. The system of claim 33, wherein the compensatory plate comprises a tilted transparent plate.

42. The system of claim 35, wherein the optical element comprises a prism.

43. A system for detecting a particle on a first surface of a transparent substrate in a medium, said substrate having a refractive index higher than that of the medium, comprising:

a radiation source operable to emit radiation;

an objective operable to focus the radiation into a radiation beam and mounted to direct the radiation beam onto a second surface of the substrate so that at least a portion of the radiation beam penetrates the substrate and traverses the first surface at an incidence angle such that there is substantially no total internal reflection of the beam by the first surface; and a detector device positioned to detect radiation from the first surface.

44. A system for detecting a particle on a first surface of a transparent substrate, comprising:

a radiation source operable to emit radiation;

an objective operable to focus the radiation into a radiation beam and mounted to direct the radiation beam onto a second surface of the substrate so that at least a portion of the radiation beam penetrates the substrate and traverses the first surface;

a detector device positioned to detect radiation from the first surface; and a compensatory plate operable to correct aberration introduced by the substrate.

45. The system of claim 43, further comprising a collector operable to collect radiation and focus the radiation onto the detector.

46. The system of claim 43, wherein the radiation source is provided by a laser source.

47. A system for detecting a particle on a first surface of a transparent substrate, comprising:

a radiation source operable to emit radiation;

an objective operable to focus the radiation into a radiation beam and mounted to direct the radiation beam onto a second surface of the substrate so that at least a portion of the radiation beam penetrates the substrate and traverses the first surface; and a detector device positioned to detect radiation from the first surface, wherein the compensatory plate comprises a tilted transparent plate.

* * * * *

UNITED STATES PATENT AND TRADEMARK OFFICE
CERTIFICATE OF CORRECTION

PATENT NO.     : 6,577,389 B2
DATED          : September 13, 2004
INVENTOR(S)    : Steve Biellak, Noah Bareket and Stanley Stokowski It is certified that error appears in the above-identified patent and that said Letters Patent is hereby corrected as shown below:

Column 1,
Line 4, before "BACKGROUND" insert the following paragraph:
-- The U.S. Government has a paid-up license in this invention and the right in limited circumstances to require the patent owner to license others on reasonable terms as provided for by the terms of contract number ATP 98-06 awarded by the National Institute of Standards and Technology (NIST). --

Signed and Sealed this

Nineteenth Day of October, 2004

JON W. DUDAS
*Director of the United States Patent and Trademark Office*